United States Patent [19]

Kamishita et al.

[11] Patent Number: 4,983,386

[45] Date of Patent: Jan. 8, 1991

[54] METHOD FOR INHIBITING THE DECREASE IN VISCOSITY OF GEL OINTMENT BASE AND OINTMENT

[75] Inventors: Takuzo Kamishita, Takatsuki; Takashi Miyazaki, Toyama; Yoshihide Okuno, Namerikawa, all of Japan

[73] Assignee: Toko Yakuhin Kogyo Kabushiki Kaisha, Osaka, Japan

[21] Appl. No.: 346,541

[22] Filed: May 1, 1989

Related U.S. Application Data

[62] Division of Ser. No. 139,806, Dec. 30, 1987.

[30] Foreign Application Priority Data

Jan. 14, 1987 [JP] Japan .................. 62-007044

[51] Int. Cl.$^5$ .................. A61K 31/74; A61K 31/78
[52] U.S. Cl. .......................... 424/78; 424/81
[58] Field of Search .................. 424/78, 81

[56] References Cited

FOREIGN PATENT DOCUMENTS 0067658 12/1982 European Pat. Off. .
0104037 3/1984 European Pat. Off. .
0162007 11/1985 European Pat. Off. .
2007091 5/1979 United Kingdom .

*Primary Examiner*—Johnnie R. Brown
*Assistant Examiner*—Carmen Pili-Curtis
*Attorney, Agent, or Firm*—Wegner, Cantor, Mueller & Player

[57] ABSTRACT

A gel ointment base having stable viscosity and resistant to a light which comprises an aqueous carboxyvinyl polymer solution and an amino acid in an amount effective for increasing the viscosity of the aqueous carboxyvinyl polymer solution, and a gel ointment comprises an active medical substance and the gel ointment base as set forth above, which has stable viscosity and resistant to a light at a pH range which does not give any irritation to viscous membranes and skins.

5 Claims, No Drawings

METHOD FOR INHIBITING THE DECREASE IN VISCOSITY OF GEL OINTMENT BASE AND OINTMENT

This application is a divisional of Ser. No. 139,806, filed Dec. 30, 1987.

This invention relates to a novel gel ointment base and a gel ointment which is a mixture of said gel ointment base and an active ingredient, more particularly, to a gel ointment base which is prepared by increasing the viscosity of an aqueous carboxyvinyl polymer solution with an amino acid, and a gel ointment which is prepared by admixing the base with an active ingredient and is suitable for applying to mucous membranes (e.g. eye, nasal cavity, oral cavity, rectum, vagina, urethra) and skin.

TECHNICAL BACKGROUND

A gel base prepared by increasing the viscosity of an aqueous carboxyvinyl polymer solution with a basic viscosity-increasing agent such as sodium hydroxide, triethanolamine, diisopropanolamine, etc. has such excellent characteristics that (i) since the stock polymer has a high purity and uniform quality, it can give a topical preparation with a high reproducibility, (ii) it shows almost a constant viscosity in the range of a temperature of from 10° to 70° C., (iii) it is hardly decomposed with microorganisms such as bacteria, (iv) the gel is stable in a wide range of pH, and the like, and hence, it has been used for preparing various topical preparations such as medicines, cosmetics, etc. However, the gel base has such defects that the viscosity thereof is decreased by irradiation with a light (ultraviolet light), and it shows low storage stability, and further that it is restricted in the utility. When the above-mentioned conventional basic viscosity-increasing agents are used, it must be adjusted to pH 10 or higher in order to eliminate the above defects. An ointment having pH 10 or higher shows high irritation to mucous membranes and skin which is not tolerable.

BRIEF SUMMARY OF THE INVENTION

The present inventors have extensively studied as to various viscosity-increasing materials suitable for increasing the viscosity of a carboxyvinyl polymer solution which can give a gel having a stable viscosity and being resistant to a light (ultraviolet: light) at a pH range which does not give any irritation to viscous membranes and skins, and it has now been found that specific amino acids can increase the viscosity of a carboxyvinyl polymer to give a gel ointment base having excellent characteristics without decreasing of the viscosity even by a light (ultraviolet light), and that a gel ointment prepared by admixing said base with an active ingredient is very excellent without decreasing of the viscosity even by a light (ultraviolet light), and then, this invention has been accomplished.

An object of this invention is to provide a gel ointment base having a stable viscosity and resistance to a light which is prepared by increasing the viscosity of an aqueous carboxyvinyl polymer solution with an amino acid. Another object of the invention is to provide a gel ointment which has a stable viscosity and being resistant to a light at a pH range which does not give any irritation to mucous membranes and skin in living bodies. These and other objects and advantages of the invention will be apparent to those skilled in the art from the following description.

BRIEF DESCRIPTION OF DRAWING

Figures show graphs of the comparison of lowering of viscosity by irradiation with a light under various test conditions as to the gel ointment base of this invention and a reference base in FIG. 1 and FIG. 2, and as to the gel ointment of this invention and a reference ointment in FIG. 3 and FIG. 4, respectively.

DETAILED DESCRIPTION OF THE INVENTION

The gel ointment base of this invention comprises an aqueous carboxyvinyl polymer solution and an amino acid of an amount effective for increasing the viscosity of the aqueous carboxyvinyl polymer solution, which can be prepared, for example, by adding an amino acid to an aqueous carboxyvinyl polymer solution with stirring and thereby mixing uniformly them, and optionally followed by adjusting to pH 4 to 9 with an appropriate pH adjustor.

The carboxyvinyl polymer used in the gel ointment base of this invention is a hydrophilic polymer which is prepared by polymerizing predominantly acrylic acid, and is commercially available in the names of Carbopol 934, ibid. 940, ibid. 941 which have been sold by Goodrich Chemical, U.S.A. The carboxyvinyl polymer is usually used in an amount of 0.05 to 5.0% by weight based on the whole weight of the composition.

The amino acid is preferably alanine, valine, isoleucine, serine, cysteine, ornithine, lysine, arginine, histidine, proline, threonine and methionine, more preferably ornithine, lysine, arginine, and proline. These amino acids are usually used in an amount of 0.1 to 10.0% by weight based on the whole weight of the composition. Other amino acids such as phenylalanine, tyrosine, aspartic acid, glutamic acid, tryptophane, asparagine, glutamine, leucine, etc. do not increase the viscosity of carboxyvinyl polymer, and although glycine shows increase of the viscosity of carboxyvinyl polymer, it is inferior to in the viscosity stability against the irradiation with a light (ultraviolet light), and hence, they are not suitable for the present invention.

The pH adjustor includes the conventional bases which are usually used as a viscosity-increasing agent, such as sodium hydroxide, potassium hydroxide, triethanolamine, diisopropanolamine, triisopropanolamine, etc. These pH adjustors are added in a minimum amount which is necessary for adjusting the pH to the desired range under taking into consideration the stability and absorbability of the active ingredient.

The gel ointment of this invention comprises an active medical substance and the gel ointment base as set forth above, which can be prepared by adding the active ingredient to the gel ointment base as prepared above and mixing them uniformly, or alternatively, depending on the active ingredient to be used, by dissolving or dispersing the active ingredient in an aqueous carboxyvinyl polymer solution, adding thereto an aqueous amino acid solution with stirring and mixing them uniformly, and optionally followed by adjusting to pH 5 to 9 with a pH adjustor.

The medical substance used as the active ingredient in this invention may be either water-soluble or water-insoluble, and is preferably stable in the preparation, i.e. in an aqueous solvent used in the step of preparation thereof.

Examples of the medical substance used for the gel ointment of this invention are hypnotics and sedatives such as glutethimide, chloral hydrate, nitrazepam, amobarbital, phenobarbital, etc.; antipyretics, analgesics and anti-inflammatory agents such as aspirin, acetaminophene, ibuprofen, flurbiprofen, indomethacin, ketoprofen, diclofenac sodium, tiaramide hydrochloride, piroxicam, flufenamic acid, mefenamic acid, pentazocine, etc.; local anaesthetics such as ethyl aminobenzoate, lidocaine, etc.; agents for ophthalmic use such as pilocarpine, physostigmine sulfate, atropine sulfate, flavine adenine dinucleotide, cyanocobalamin, naphazoline nitrate, micronomicin sulfate, fluorometholone, sodium guaiazulenesulfonate, befunolol hydrochloride, disodium cromoglicate, etc.; agents for nasal chloride, disodium cromoglicate, etc.; cardiotonics such as ubidecarenone, etc.; antiarrhythmic agents such as propranolol hydrochloride, pindolol, phenytoin, disopyramide, etc.; coronary vasodilators such as isosorbide nitrate, nifedipine, diltiazem hydrochloride, dipyridamole, etc.; agents effective for digestive organs such as domperidone, etc.; corticoids such as triamcinolone acetonide, dexamethasone, betamethasone phosphate sodium, prednisolone acetate, fluocinolide, beclomethasone propionate, etc.; antiplasmins such as tranexamic acid, etc.; fungicides such as clotrimazole, miconazole nitrate, ketoconazole, etc.; antitumor agents such as tegafur, fluorouracil, mercaptopurine, etc.; antibiotics such as amoxycillin, ampicillin, cephalexin, cephalothin sodium, ceftizoxime sodium, erythromycin, oxytetracycline hydrochloride, etc., physiological active peptides such as insulin, elcatonin, urokinase, TPA, interferon, etc., and the like. The dose of the active ingredients may vary depending on the kinds of the agents, but is usually in an amount sufficient for exhibiting the desired activity which will be apparent to those skilled in the art from the usual dosage of these available medicaments.

In case of using an active ingredient which is insoluble in water, the obtained gel ointment becomes opaque white, but the active ingredient does not precipitate, and hence, it can effectively be used. However, when it is desirable that the active ingredient is dissolved because of easier absorption into the living bodies as in case of applying to the skin, it may be dissolved with a solubilizer or it may be previously dissolved in a water-soluble organic solvent, and then it is used for the preparation. The water-soluble organic solvent includes lower alcohols (e.g. ethanol, isopropanol, etc.), and glycols (e.g. propyene glycol, 1,3-butylene glycol, polyethylene glycol having a molecular weight of 300 to 500, etc.). Besides, the solubilizer includes, for example, various surfactants, crotamiton, glycol salicylate, peppermint oil, benzyl alcohol, and the like, which are selected depending on the solubility of the active ingredients.

The gel ointment base and gel ointment of this invention have preferably a viscosity of 1,000 to 100,000 cP (centipoises). When the viscosity is lower than 1,000 cP, they have too high fluidity and hence are hardly applicable to the viscous membranes and the skins, and on the other hand, when the viscosity is higher than 100,000 cP, the preparations are too hard and hence are hardly administered. Besides, when the viscosity is lower, the active ingredient can rapidly be absorbed into the body and hence the preparation is a rapid release one, and on the other hand, when the viscosity is higher, the gel is slowly degraded and the active ingredient is slowly absorbed and hence the preparation is a sustained and delayed release one. The viscosity is somewhat affected depending on the kinds of the active ingredients to be added, but mainly depends on the concentration of carboxyvinyl polymer. In order to obtain the gel base or gel preparation having the desired viscosity, the carboxyvinyl polymer is used in an aqueous solution having a concentration thereof in the range of 0.1 to 5.0% by weight, as mentioned hereinbefore. When the viscosity is decreased by the addition of the active ingredient, an aqueous solution of carboxyvinyl polymer having a higher concentration thereof is used, and thereby, there can be obtained the desired gel having a suitable viscosity.

The gel ointment base and gel ointment of this invention show less lowering of viscosity by the irradiation of a light and hence are superior in comparison with the conventional gel ointment bases or preparations which are prepared by using conventional basic substances as a viscosity-increasing agent, as is clear from the comparative experiments as disclosed hereinafter.

The present invention is illustrated by the following Examples and Experiments, but should not be limited thereto. Hereinafter, "%" means % by weight. Besides, in this invention, the viscosity is measured by using C type viscometer (manufactured by Tokyo Keiki K.K., Japan) at 20° C.

EXAMPLE 1

Carboxyvinyl polymer (Carbopol 940) is dissolved in purified water to give a 4% aqueous carboxyvinyl polymer solution. To the aqueous solution (12.5 g) is gradually added a 4% aqueous L-arginine solution (25 g) with stirring, and thereto is added purified water so as to become totally 100 g, and the mixture is uniformly mixed to give a gel having pH 7.3 and a viscosity of 38,000 cP (the concentration of carboxyvinyl polymer: 0.5%).

In the same manner as described above except that the concentration of carboxyvinyl polymer is varied (the amount of L-arginine is double of that of carboxyvinyl polymer), there are prepared gels having the following viscosities.

| Concentration of carboxyvinyl polymer (%) | Viscosity (cP) |
| --- | --- |
| 4.0 | 120,000 |
| 3.0 | 87,000 |
| 2.0 | 72,000 |
| 1.0 | 50,000 |
| 0.50 | 38,000 |
| 0.25 | 29,000 |
| 0.10 | 10,000 |

EXAMPLE 2

To the 4% aqueous carboxyvinyl polymer solution (30.0 g) as prepared in Example 1 is gradually added a 4% aqueous L-arginine solution (60 g) with stirring and thereto is further added purified water so as to become totally 100 g. The mixture is uniformly stirred to give a gel having pH 6.7 and a viscosity of 56,000 cP (the concentration of carboxyvinyl polymer: 1.2%).

In the same manner as described above except that other amino acids are used instead of L-arginine (the amount of the amino acids is double of that of carboxyvinyl polymer) and the concentration of carboxyvinyl polymer is 1.2%, there are prepared gels having the following viscosities.

| Amino acid (addition amount: 2.4%) | Viscosity (cP) |
| --- | --- |
| L-arginine | 56,000 |
| L-alanine | 50,000 |
| L-serine | 48,000 |
| L-histidine | 55,000 |
| L-proline | 49,000 |
| L-valine | 48,000 |

EXAMPLE 3

To a 4% aqueous carboxyvinyl polymer solution (25.0 g) is gradually added a 4% aqueous L-alanine solution (25 g) with stirring to increase the viscosity and further is added a 2% aqueous sodium hydroxide solution (20.0 g), and the mixture is stirred and thereto is further added purified water so as to become totally 100 g. The mixture is uniformly stirred to give a gel having pH 7.3 and a viscosity of 48,500 cP (the concentration of carboxyvinyl polymer: 1.0%).

EXAMPLE 4

To a 4% aqueous carboxyvinyl polymer solution (12.5 g) is gradually added a 4% aqueous L-lysine solution (12.5 g) with stirring to increase the viscosity and further is added a 2% aqueous triethanolamine solution (17.5 g), and the mixture is stirred and thereto is further added purified water so as to become totally 100 g. The mixture is uniformly stirred to give a gel having pH 7.5 and a viscosity of 41,000 cP (the concentration of carboxyvinyl polymer: 0.5%).

EXAMPLE 5

Eye drops of disodium cromoglicate (2.0%):

| Materials | Amount (%) |
| --- | --- |
| disodium cromoglicate | 2.0 |
| 1% aqueous carboxyvinyl polymer solution | 25.0 |
| 2% aqueous L-arginine solution | 25.0 |
| purified water | 48.0 |

To a 1% aqueous carboxyvinyl polymer solution is gradually added a 2% aqueous L-arginine solution and the mixture is stirred to increase the viscosity to give a gel. To the gel is added disodium cromoglicate, and the mixture is uniformly stirred to give a gel preparation (pH 7.3, viscosity 1,100 cP).

EXAMPLE 6

Nasal drops of disodium cromoglicate (2.0%):

| Materials | Amount (%) |
| --- | --- |
| disodium cromoglicate | 2.0 |
| 2% aqueous carboxyvinyl polymer solution | 25.0 |
| 2% aqueous L-serine solution | 25.0 |
| 2% aqueous sodium hydroxide solution | 10.0 |
| purified water | 38.0 |

To a 2% aqueous carboxyvinyl polymer solution is gradually added a 2% aqueous L-serine solution and the mixture is stirred to increase the viscosity to give a gel. The pH is adjusted with a 2% aqueous sodium hydroxide solution, and thereto is added disodium cromoglicate, and the mixture is uniformly stirred to give a gel preparation (pH 7.4, viscosity 8,200 cP).

EXAMPLE 7

Lectal infusion preparation of insulin (10 U/g):

| Materials | Amount (%) |
| --- | --- |
| insulin | 0.0377 |
| 4% aqueous carboxyvinyl polymer solution | 25.0 |
| 4% aqueous L-lysine solution | 50.0 |
| purified water | 24.9623 |

To a 4% aqueous carboxyvinyl polymer solution is gradually added a 4% aqueous L-lysine solution with stirring and the mixture is continuously stirred to give a gel. To the gel is added a suspension of insulin in purified water, and the mixture is uniformly stirred to give a gel preparation (pH 6.8, viscosity 26,100 cP).

EXAMPLE 8

Rectal infusion preparation of diltiazem hydrochloride (1.0%):

| Materials | Amount (%) |
| --- | --- |
| diltiazem hydrochloride | 1.0 |
| 4% aqueous carboxyvinyl polymer solution | 12.5 |
| 4% aqueous L-valine solution | 25.0 |
| 2% aqueous sodium hydroxide solution | 10.0 |
| purified water | 51.5 |

To a 4% aqueous carboxyvinyl polymer solution is added purified water and thereto is gradually added diltiazem hydrochloride with stirring. To the mixture is gradually added a 4% aqueous L-valine solution and the mixture is uniformly stirred to increase the viscosity and thereto is gradually added a 2% aqueous sodium hydroxide solution. The mixture is stirred to give a gel preparation (pH 6.9, viscosity 10,000 cP).

EXAMPLE 9

Rectal infusion preparation of diclofenac sodium (2.5%):

| Materials | Amount (%) |
| --- | --- |
| diclofenac sodium | 2.5 |
| 4% aqueous carboxyvinyl polymer solution | 12.5 |
| 4% aqueous L-arginine solution | 50.0 |
| purified water | 35.0 |

To a 4% aqueous carboxyvinyl polymer solution is gradually added a 4% aqueous L-arginine solution with stirring and the mixture is continuously stirred to give a gel. To the gel is added a solution of diclofenac sodium in purified water and the mixture is uniformly stirred to give a gel preparation (pH 7.2, viscosity 8,000 cP).

EXAMPLE 10

Eye drops of ketoprofen (0.1%):

| Materials | Amount (%) |
| --- | --- |
| ketoprofen | 0.1 |
| 1% aqueous carboxyvinyl polymer solution | 20.0 |

| Materials | Amount (%) |
|---|---|
| 1% aqueous L-proline solution | 40.0 |
| 2% aqueous sodium hydroxide solution | 16.0 |
| purified water | 23.9 |

To a 1% aqueous carboxyvinyl polymer solution is gradually added a 1% aqueous L-proline solution with stirring and the mixture is continuously stirred to give a gel. To the gel are added a 2% aqueous sodium hydroxide solution and a solution of ketoprofen in purified water, and the mixture is uniformly stirred to give a gel preparation (pH 7.8, viscosity 1,000 cP).

EXPERIMENT 1

As to the gel ointment bases and gel ointments of this invention and reference bases and reference preparations which were prepared in the same manner as described above except that a conventional viscosity-increasing agents (sodium hydroxide, triethanolamine) is used, there were compared the lowering of viscosity by irradiation with a light in a transparent glass vessel.

The test conditions (i to v) are shown in the following table.

The results are shown in Tables 1 to 5 and FIG. 1 to FIG. 4. In the tables, the carboxyvinyl polymer is represented by "CVP", and the results are shown by the found viscosity at a time after being elapsed for a certain period of time from the initiation of test, and the viscosity retention rate compared with the initial viscosity is also shown within a parenthesis.

Test conditions

| No. | Samples | Active ingredient | Light-irradiation | Concentration of CVP (%) | Results |
|---|---|---|---|---|---|
| i | Base | — | Room diffused light | 0.5 | Table 1 & FIG. 1 |
| ii | " | — | Direct sun light | 0.25 | Table 2 & FIG. 2 |
| iii | " | — | Direct sun light | 1.0 | Table 3 |
| iv | Ointment | Tranexamic acid | Direct sun light | " | Table 4 & FIG. 3 |
| v | " | Ketoprofen | Direct sun light | " | Table 5 & FIG. 4 |

TABLE 1

| Sample No. | Formulation | | Initial viscosity | After 1 week | After 2 weeks | After 3 weeks |
|---|---|---|---|---|---|---|
| 1 | CVP | 0.5% | 40,000 cP | 36,000 cP | 33,600 cP | 30,500 cP |
|  | L-Arginine | 1.0% | (100.0%) | (90.0%) | (84.0%) | (76.3%) |
|  | Purified water | 98.5% | | | | |
| 2 | CVP | 0.5% | 40,000 cP | 24,000 cP | 15,000 cP | 8,500 cP |
|  | NaOH | 0.02% | (100.0%) | (60.0%) | (37.5%) | (21.3%) |
|  | Purified water | 99.48% | | | | |

TABLE 2

| Sample No. | Formulation | | Initial viscosity | After 1 day | After 3 days | After 5 days | After 7 days | After 14 days |
|---|---|---|---|---|---|---|---|---|
| 3 | CVP | 0.25% | 29,000 cP | 28,000 cP | 26,500 cP | 25,000 cP | 23,500 cP | 20,000 cP |
|  | L-arginine | 0.50% | (100.0%) | (96.6%) | (91.4%) | (86.2%) | (81.0%) | (69.0%) |
|  | Purified water | 99.25% | | | | | | |
| 4 | CVP | 0.25% | 26,500 cP | 23,000 cP | 18,000 cP | 14,000 cP | 11,500 cP | 4,900 cP |
|  | NaOH | 0.10% | (100.0%) | (86.8%) | (67.9%) | (52.8%) | (43.4%) | (18.5%) |
|  | Purified water | 99.65% | | | | | | |
| 5 | CVP | 0.25% | 31,000 cP | 29,000 cP | 25,500 cP | 22,500 cP | 18,000 cP | 11,500 cP |
|  | Triethanolamine | 0.35% | (100.0%) | (93.5%) | (82.3%) | (72.6%) | (58.1%) | (37.1%) |
|  | Purified water | 99.40% | | | | | | |
| 6 | CVP | 0.25% | 27,000 cP | 25,000 cP | 23,500 cP | 21,500 cP | 19,500 cP | 15,000 cP |
|  | L-arginine | 0.25% | (100.0%) | (92.6%) | (87.0%) | (79.6%) | (72.2%) | (55.6%) |
|  | NaOH | 0.05% | | | | | | |
|  | Purfied water | 99.45% | | | | | | |

TABLE 3

| Sample No. | Viscosity-increasing agent | Formulation | | Initial viscosity | After one week |
|---|---|---|---|---|---|
| 7 | Not added | CVP | 1.0% | 3,000 cP | 3,000 cp |
|  |  | Purified water | 99.0% | | (100.0%) |
| 8 | Sodium hydroxide | CVP | 1.0% | 55,000 cp | 9,000 cp |
|  |  | NaOH | 0.4% | | (16.4%) |
|  |  | Purified water | 98.6% | | |
| 9 | Triethanolmine | CVP | 1.0% | 56,000 cp | 18,000 cp |
|  |  | TEA | 1.4% | | (32.1%) |
|  |  | Purified water | 97.6% | | |
| 10 | Glycine | CVP | 1.0% | 45,000 cp | 15,500 cp |
|  |  | Gly. | 2.0% | | (34.4%) |
|  |  | Purified water | 97.0% | | |
| 11 | Alanine | CVP | 1.0% | 44,000 cp | 27,000 cp |
|  |  | Ala. | 2.0% | | (61.4%) |
|  |  | Purified water | 97.0% | | |
| 12 | Valine | CVP | 1.0% | 44,000 cp | 16,500 cp |
|  |  | Val. | 2.0% | | (60.2%) |
|  |  | Purified water | 97.0% | | |

TABLE 3-continued

| Sample No. | Viscosity-increasing agent | Formulation | | Initial viscosity | After one week |
|---|---|---|---|---|---|
| 13 | Isoleucine | CVP | 1.0% | 37,000 cp | 22,500 cp (60.8%) |
| | | Ile. | 2.0% | | |
| | | Purified water | 97.0% | | |
| 14 | Serine | CVP | 1.0% | 38,000 cp | 24,000 cp (63.2%) |
| | | Ser. | 2.0% | | |
| | | Purified water | 97.0% | | |
| 15 | Cysteine | CVP | 1.0% | 37,000 cp | 23,000 cp (62.2%) |
| | | Cys. | 2.0% | | |
| | | Purified water | 97.0% | | |
| 16 | Ornithine | CVP | 1.0% | 48,000 cp | 29,500 cp (61.5%) |
| | | Orn. | 2.0% | | |
| | | Purified water | 97.0% | | |
| 17 | Lysine | CVP | 1.0% | 47,000 cp | 29,000 cp (61.7%) |
| | | Lys. | 2.0% | | |
| | | Purified water | 97.0% | | |
| 18 | Arginine | CVP | 1.0% | 51,000 cp | 31,000 cp (60.8%) |
| | | Arg. | 2.0% | | |
| | | Purified water | 97.0% | | |
| 19 | Histidine | CVP | 1.0% | 48,500 cp | 30,000 cp (61.9%) |
| | | His. | 2.0% | | |
| | | Purified water | 97.0% | | |
| 20 | Proline | CVP | 1.0% | 43,000 cp | 26,500 cp (61.6%) |
| | | Pro. | 2.0% | | |
| | | Purified water | 97.0% | | |
| 21 | Threonine | CVP | 1.0% | 36,000 cp | 22,000 cp (61.1%) |
| | | Thr. | 2.0% | | |
| | | Purified water | 97.0% | | |
| 22 | Methionine | CVP | 1.0% | 36,000 cp | 22,000 cp (61.1%) |
| | | Met. | 2.0% | | |
| | | Purified water | 97.0% | | |
| 23 | Valine Sodium hydroxide | CVP | 1.0% | 47,000 cp | 27,500 cp (58.5%) |
| | | Val. | 1.0% | | |
| | | NaOH | 0.2% | | |
| | | Purified water | 97.8% | | |
| 24 | Proline Triethanolamine | CVP | 1.0% | 48,000 cp | 28,500 cp (59.4%) |
| | | Pro. | 1.0% | | |
| | | TEA | 0.7% | | |
| | | Purified water | 97.3% | | |
| 25 | Alanine Arginine | CVP | 1.0% | 47,000 cp | 26,000 cp (55.3%) |
| | | Ala. | 1.0% | | |
| | | Arg. | 1.0% | | |
| | | Purified water | 97.0% | | |

TABLE 4

| Sample No. | Formulation | | Initial viscosity | After 3 days | After 6 days | After 9 days |
|---|---|---|---|---|---|---|
| 26 | Tranexamic acid | 1.0% | 40,000 cP (100.0%) | 39,000 cP (97.5%) | 30,500 cP (76.3%) | 27,000 cP (67.5%) |
| | CVP | 1.0% | | | | |
| | L-Arginine | 2.0% | | | | |
| | Purified water | 96.0% | | | | |
| 27 | Tranexamic acid | 1.0% | 39,000 cP (100.0%) | 35,000 cP (89.7%) | 23,000 cP (59.0%) | 16,500 cP (42.3%) |
| | CVP | 1.0% | | | | |
| | NaOH | 0.4% | | | | |
| | Purified water | 97.6% | | | | |

TABLE 5

| Sample No. | Formulation | | Initial viscosity | After 3 days | After 6 days | After 9 days |
|---|---|---|---|---|---|---|
| 28 | Ketoprofen | 3.75% | 36,000 cP (100.0%) | 35,000 cP (97.2%) | 29,500 cP (81.9%) | 25,500 cP (70.8%) |
| | CVP | 1.00% | | | | |
| | L-Arginine | 5.00% | | | | |
| | Purified water | 90.25% | | | | |
| 29 | Ketoprofen | 3.75% | 35,000 cP (100.0%) | 30,500 cP (87.1%) | 18,000 cP (51.4%) | 12,500 cP (35.7%) |
| | CVP | 1.00% | | | | |
| | NaOH | 1.00% | | | | |
| | Purified water | 94.25% | | | | |
| 30 | Ketoprofen | 3.75% | 38,000 cP (100.0%) | 35,000 cP (92.1%) | 24,000 cP (63.2%) | 17,000 cP (44.7%) |
| | CVP | 1.00% | | | | |
| | Triethanolamine | 3.50% | | | | |
| | Purified water | 91.75% | | | | |

What is claimed is:

1. A method for inhibiting a decrease in viscosity of a gel ointment base comprising an aqueous carboxyvinyl polymer solution, said method comprising adding to the solution an amino acid selected from the group consisting of alanine, valine, isoleucine, serine, cysteine, ornithine, lysine, arginine, histidine, proline, threonine, and methionine in an amount effective for inhibiting the decrease in viscosity of the base due to irradiation by light, wherein the base is adjusted to a pH of about 5-9 and a viscosity of about 1,000-100,000 cP at 20° C.

2. A method for inhibiting a decrease in viscosity of a gel ointment comprising an aqueous carboxyvinyl polymer solution and an effective amount of an active medical substance, said method comprising adding to the solution an amino acid selected from the group consisting of alanine, valine, isoleucine, serine, cysteine, ornithine, lysine, arginine, histidine, proline, threonine, and methionine in an amount effective for inhibiting the decrease in viscosity of the base due to irradiation by light, wherein the base is adjusted to a pH of about 5-9 and a viscosity of about 1,000-100,000 cP at 20° C.

3. The method according to claim 2, wherein the aqueous carboxyvinyl polymer solution is an aqueous solution containing 0.05-5.0% by weight of a carboxyvinyl polymer.

4. The method according to claim 2, wherein the amino acid is used in an amount of 0.1 to 10.0% by weight based on the whole weight of the ointment.

5. The method according to claim 2, wherein a solubilizer or a solvent is further contained in order to dissolve the active medical substance.

* * * * *